United States Patent
Brakhage et al.

(10) Patent No.: US 9,062,077 B2
(45) Date of Patent: Jun. 23, 2015

(54) BENZOPYRANOBENZOTHIAZINONES AND THEIR USE AS FUNGICIDES, ANTIBIOTICS AND ANTITUMOR AGENTS

(75) Inventors: Axel Brakhage, Weimar (DE); Hans-Martin Dahse, Jena (DE); Christian Hertweck, Leipzig (DE); Hans-Wilhelm Nuetzmann, Hohen Wangelin (DE); Kirstin Scherlach, Leipzig (DE)

(73) Assignee: Leibniz-Institut fuer Naturstoff-Forschung und Infektionsbiologie E.V. Hans-Knoell-Institute (HKI), Jena (DE)

( * ) Notice: Subject to any disclaimer, the term of this patent is extended or adjusted under 35 U.S.C. 154(b) by 0 days.

(21) Appl. No.: 14/128,095

(22) PCT Filed: Jun. 15, 2012

(86) PCT No.: PCT/EP2012/002534
§ 371 (c)(1),
(2), (4) Date: May 2, 2014

(87) PCT Pub. No.: WO2013/000543
PCT Pub. Date: Jan. 3, 2013

(65) Prior Publication Data
US 2014/0315896 A1 Oct. 23, 2014

(30) Foreign Application Priority Data
Jun. 28, 2011 (EP) ..................................... 11005242

(51) Int. Cl.
*C07D 513/04* (2006.01)
(52) U.S. Cl.
CPC .................................... *C07D 513/04* (2013.01)
(58) Field of Classification Search
CPC .................................................... C07D 513/04
USPC .................................... 544/14; 514/224.5
See application file for complete search history.

(56) References Cited

PUBLICATIONS

Sucharita et al. Sulfur Letters, vol. 2(5), Oct. 1984, pp. 183-188.*
Reddy, B.S. and Darbarwar, M. "Synthesis and Physiological Activity of 7H-[1] Benzopyrano [4,3-b] [1,4]-Benzothiazin-6-ones" Sulfur Letters 1984 2(5):183-188.
Scherlach et al. "Cytotoxic Pheofungins from an Engineered Fungus Impaired in Posttranslational Protein Modification" Angewandte Chemie International Edition 2011 50:9843-9847.
Shah et al. "Biological Activity of 6,12-Dihydro-1-Benzopyrano [3,4-*b*] [1,4] benzothiazin-6-ones" Anticancer Research 1998 18:61-64.
International Search Report from PCT/EP2012/002534, Aug. 14, 2012, PCT.
International Preliminary Report on Patentability from PCT/EP2012/002534, Jan. 7, 2014, PCT.
Abdou et al. "Botryorhodines A-D, Antifungal and Cytotoxic Depsidones from *Botryosphaeria rhodina*, an Endophyte of the Medicinal Plant *Bidens pilosa*" Phytochemistry 2010 71:110-116.
Ballance, D.J. and Turner, G. "Development of a High-Frequency Transforming Vector for *Aspergillus nidulans*" Gene 1985 36:321-331.
Bergmann et al. "Genomics-Driven Discovery of PKS-NRPS Hybrid Metabolites from *Aspergillus nidulans*" Nature Chemical Biology 2007 3(4):213-217.
Bergmann et al. "Activation of a Silent Fungal Polyketide Biosynthesis Pathway through Regulatory Cross Talk with a Cryptic Nonribosomal Peptide Synthetase Gene Cluster" Applied and Environmental Microbiology 2010 76(24):8143-8149.
Bok et al. "Chromatin-Level Regulation of Biosynthetic Gene Clusters" Nature Chemical Biology 2009 5(7):462-464.
Fisch et al. "Chemical Induction of Silent Biosynthetic Pathway Transcription in *Aspergillus niger*" Journal of Industrial Microbiology and Biotechnology 2009 36:1199-1213.
Henrikson et al. "A Chemical Epigenetics Approach for Engineering the in situ Biosynthesis of a Cryptic Natural Product from *Aspergillus niger*" Organic & Biomolecular Chemistry 2009 7:435-438.
Krauth et al. "Synthesis and Characterization of Novel 1,2,3-Triazine Derivatives with Antiproliferative Activity" Bioorganic & Medicinal Chemistry 2010 18:1816-1821.
Lipman, A. G. "Martindale: 'Martindale—the Extra Pharmacopoeia' (30th ed), edited by J. E. F. Reynolds" The International Journal of Pharmacy Practice 1993 2(2):124.
Nahlik et al. "The COP9 Signalosome Mediates Transcriptional and Metabolic Response to Hormones, Oxidative Stress Protection and Cell Wall Rearrangement During Fungal Development" Molecular Microbiology 2010 78(4):964-979.
Scherlac, K. and Hertweck, C. "Triggering Cryptic Natural Product Biosynthesis in Microorganisms" Organic & Biomolecular Chemistry 2009 7:1753-1760.
Schroeckh et al. "Intimate Bacterial-Fungal Interaction Triggers Biosynthesis of Archetypal Polyketides in *Aspergillus nidulans*" Proceedings of the National Academy of Sciences 2009 106(34):14558-14563.

(Continued)

*Primary Examiner* — Kahsay Habte
(74) *Attorney, Agent, or Firm* — Licata & Tyrrell P.C.

(57) ABSTRACT

This invention relates to the field of biologically active compounds and specifically to phaeofungins, of the general formula (I) or a pharmacologically acceptable salt, solvate, hydrate or a pharmacologically acceptable formulation thereof, pharmaceutical compositions comprising these compounds, methods for the production of the phaeofungins and their use as fungicide, antibiotic as well as antitumor agent.

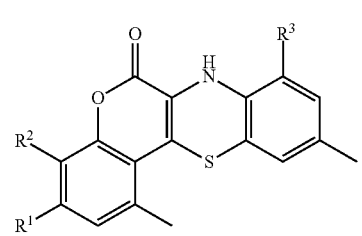

(I)

12 Claims, 4 Drawing Sheets

(56) References Cited

PUBLICATIONS

Shwab, E. K. and Keller, N. P. "Regulation of Secondary Metabolite Production in Filamentous Ascomycetes" Mycological Research 2008 112:225-230.

Shwab et al. "Histone Deacetylase Activity Regulates Chemical Diversity in *Aspergillus*" Eukaryotic Cell 2007 6(9):1656-1664.

Szewcyzk et al. "Fusion PCR and Gene Targeting in *Aspergillus nidulans*" Nature Protocols 2006 1(6):3111-3121.

Tüncher et al. "The CCAAT-binding Complex of Eukaryotes: Evolution of a Second NLS in the HapB Subunit of the Filamentous Fungus *Aspergillus nidulans* Despite Functional Conservation at the Molecular Level between Yeast, *A. nidulans* and Human" Journal of Molecular Biology 2005 352:517-533.

von Nussbaum et al. "Antibacterial Natural Products in Medicinal Chemistry—Exodus or Revival?" Angewandte Chemie International Edition 2006 45:5072-5129.

Weist, S. and Süssmuth, R. D. "Mutational Biosynthesis—a Tool for the Generation of Structural Diversity in the Biosynthesis of Antibiotics" Applied Microbiology and Biotechnology 2005 68:141-150.

Wickes, B. "DNA Isolation from a Filamentous Fungus Using the MasterPure™ Yeast DNA Purification Kit" Epicentre Forum 2004 11(6):7.

Williams et al. "Epigenetic Remodeling of the Fungal Secondary Metabolome" Organic & Biomolecular Chemistry 2008 6:1895-1897.

Winter et al. "Genomics-Inspired Discovery of Natural Products" Current Opinion in Chemical Biology 2011 15:22-31.

\* cited by examiner

A

B

BENZOPYRANOBENZOTHIAZINONES AND THEIR USE AS FUNGICIDES, ANTIBIOTICS AND ANTITUMOR AGENTS

This application is a U.S. National Stage Application of PCT/EP2012/002534 filed Jun. 15, 2012, which claims priority from EPO Application No. 11005242.0 filed Jun. 28, 2011, the contents of each of which are incorporated herein by reference in their entirety.

This invention relates to the field of biologically active compounds and specifically to phaeofungins, pharmaceutical compositions comprising these compounds, methods for the production of the phaeofungins and their use as fungicide, antibiotic as well as antitumor agent.

Fungi produce a multitude of natural products that have a major impact on ecology, agriculture, and health. While traditional natural product research has provided a vast array of chemically and functionally diverse compounds, it appears that still most of the biosynthetic potential is hidden and thus has been overlooked. Indeed, analyses of fully sequenced fungal genomes revealed that the number of encoded biosynthetic pathways by far exceeds the range of metabolites observed under standardized cultivation in the laboratory (J. M. Winter, S. Behnken, C. Hertweck, *Curr. Opin. Chem. Biol.* 2011, 15, 22). The reason for this observation is that most biosynthesis genes remain silent, and a major challenge is to explore ways to activate these cryptic pathways. A growing body of data illustrates that the variation of culture conditions and environmental factors including microbial interactions may dramatically influence the metabolite patterns of microorganims (K. Scherlach, C. Hertweck, *Org. Biomol. Chem.* 2009, 7, 1753). To control the production of secondary metabolites at certain developmental stages or under specific environmental conditions, fungi employ a finely tuned system of global and specific regulatory mechanisms (Shwab and Keller, *Mycol. Res.* 2008, 112, 225; Bergmann of al., *Nat. Chem. Biol.* 2007, 3, 213; Bergmann et al., *Appl. Environ. Microbiol.* 2010, 76, 8143; Bok et al., *Nat. Chem. Biol.* 2009, 5, 462). These specific regulatory mechanisms prevent fungi from wasting their energy for the production of molecules, e.g. secondary metabolites, which are not essential for their survival. Thus, the requisite biosynthesis gene clusters remain silent in the absence of environmental cues or particular triggers. In order to yield "cryptic natural products" external cues, co-cultivation and genomic approaches such as genome-mining, epigenetic remodeling, and engineered pathway activation have been employed.

For example, it has been demonstrated that the deletion of genes encoding an *Aspergillus nidulans* histone deacetylase (HDAC), hdaA, as well as the treatment of fungal cultures with HDAC inhibitors caused transcriptional activation of secondary metabolite gene clusters and production of several natural compounds (Fisch at al., *J. Ind. Microbiol. Biotechnol.* 2009, 36, 1199; Henrikson et al., *Org. Biomol. Chem.* 2009, 7, 435; Shwab of al., *Eukaryot. Cell* 2007, 6, 1656; Williams at al., *Org. Biomol. Chem.* 2008, 6, 1895). It has also been shown that manipulation of the COP9 signalosome, a crucial regulator of ubiquitin ligases, results in an altered transcriptional and metabolic response (Nahlik et al., *Mol. Microbiol.* 2010, 78, 964).

Microbial natural products are one of the most promising sources for novel antibiotics, fungicides as well as antitumor agents. This is, because natural products own an element of structural complexity which is required for the inhibition of many bacterial, fungal or vertebrate protein targets. Moreover, there is a rapid decline in the effectiveness of antibiotics and fungicides due to the emergence of resistance to many antibacterial and antifungal agents, respectively. Similarly, there hardly exist effective therapies for the treatment of cancer. Accordingly, there is a need for a constant supply of new antibiotics and fungicides for effective treatment of bacterial and fungal infections as well as for novel compounds having antitumor activity.

Therefore, the problem underlying the present invention is to provide novel compounds having antibacterial, antifungal and/or antitumor activity. In particular, phaeofungins are provided, especially a hitherto fully unprecedented type of benzopyranobenzothiazinones secondary metabolites from *A. nidulans* ΔnnaB mutant with a chromophore that is remarkably similar to pheomelanins, the red pigments in human hair of Celtic origin.

The present invention relates to a compound, namely a phaeofungin of the general formula (I):

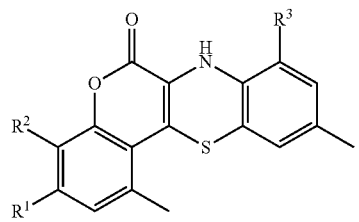

or a pharmacologically acceptable salt, solvate, hydrate or a pharmacologically acceptable formulation thereof, wherein $R^1$ is a hydrogen atom, a halogen atom, a hydroxy, a nitro, a cyano, an amino, a mercapto, an alkyl, an alkenyl, an alkinyl, a heteroalkyl, a cycloalkyl, a heterocycloalkyl, an alkylcycloalkyl, a heteroalkylcycloalkyl, an aryl, a heteroaryl, an aralkyl or a heteroaralkyl group, wherein the alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group can be substituted with from 1 to 3 substituents which substituents are each independently selected from halogen atom, hydroxy, nitro, amino, alkoxy, carboxyl, alkyl, alkynyl, alkenyl, aryl, sulfonyl, phosphoryl, or $R^1$ is taken together with $R^2$ to form a 5- to 8-membered carbocyclic or heterocyclic ring that is substituted with from 0 to 3 substituents which substituents are each independently selected from halogen atom, hydroxy, nitro, amino, alkoxy, carboxyl, alkyl, alkynyl, alkenyl, or aryl;

$R^2$ is a hydrogen atom, a halogen atom, a hydroxy, an amino, a mercapto, an alkyl, an alkenyl, an alkinyl, a heteroalkyl, a cycloalkyl, a heterocycloalkyl, an alkylcycloalkyl, a heteroalkylcycloalkyl, an aryl, a heteroaryl, an aralkyl or a heteroaralkyl group, wherein the alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group can be substituted with from 1 to 3 substituents which substituents are each independently selected from halogen atom, hydroxy, nitro, amino, alkoxy, carboxyl, alkyl, alkynyl, alkenyl, aryl, sulfonyl, phosphoryl;

$R^3$ is a hydrogen atom, a halogen atom, a hydroxy, a nitro, a cyano, an amino, a mercapto, an alkyl, an alkenyl, an alkinyl, a heteroalkyl, a cycloalkyl, a heterocycloalkyl, an alkylcycloalkyl, a heteroalkylcycloalkyl, an aryl, a heteroaryl, an aralkyl or a heteroaralkyl group, wherein the alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group can be substituted with from 1 to 3 substituents which substituents are each independently selected from halogen atom, hydroxy, nitro, amino, alkoxy, carboxyl, alkyl, alkynyl, alkenyl, aryl, sulfonyl, or phosphoryl.

Compounds are generally described herein using standard nomenclature. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example, a chiral HPLC column.

Compounds herein may also be described using a general formula that includes variables such as, e.g., A, $R^1$-$R^6$, Y, etc. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups and R* at each occurrence is selected independently from the definition of R*. Also, combinations of substituents and/or variables are permissible only if such combinations result in stable compounds, i.e., compounds that can be isolated, characterized and tested for biological activity.

A "pharmaceutically acceptable salt" of a compound disclosed herein preferably is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC-(CH_2)_n-COOH$ where n is any integer from 0 to 4, i.e., 0, 1, 2, 3, or 4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

It will be apparent that each compound of formula (I) may, but need not, be present as a hydrate, solvate or non-covalent complex. In addition, the various crystal forms and polymorphs are within the scope of the present invention, as are prodrugs of the compounds of formula (I) provided herein.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "substituent," as used herein, refers to a molecular moiety that is covalently bonded to an atom within a molecule of interest, e.g. to a compound of general formula (I) or a prodrug thereof. For example, a "ring substituent" may be a moiety such as a halogen, alkyl group, haloalkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

The expression alkyl preferably refers to a saturated, straight-chain or branched hydrocarbon group that contains from 1 to 20 carbon atoms, preferably from 1 to 12 carbon atoms, more preferably from 1 to 6 carbon atoms, for example a methyl, ethyl, propyl, iso-propyl, n-butyl, iso-butyl, sec-butyl, tert-butyl, n-pentyl, n-hexyl, 2,2-dimethylbutyl or n-octyl group.

The expressions alkenyl and alkynyl refer to at least partially unsaturated, straight-chain or branched hydrocarbon groups that contain from 2 to 20 carbon atoms, preferably from 2 to 12 carbon atoms, more preferably from 2 to 6 carbon atoms, for example an ethenyl, allyl, acetoxylenyl, propargyl, isoprenyl or hex-2-enyl group. Preferably, alkenyl groups have one or two, more preferably one, double bond(s) and alkynyl groups have one or two, more preferably one, triple bond(s).

The expression heteroalkyl preferably refers to an alkyl, alkenyl or alkynyl group, for example heteroalkenyl, heteroalkynyl, in which one or more, preferably 1, 2 or 3 carbon atoms have been replaced each independently of the others by an oxygen, nitrogen, phosphorus, boron, selenium, silicon or sulphur atom, preferably oxygen, sulphur or nitrogen. The expression heteroalkyl, for example, refers to an alkoxy group. Furthermore, heteroalkyl preferably refers to a carboxylic acid or to a group derived from a carboxylic acid such as, for example, acyl, acylalkyl, alkoxycarbonyl, acyloxy, acyloxyalkyl, carboxyalkylamide, alkylcarbamoylalkyl, alkylcarbamoyloxyalkyl, alkylureidoalkyl, or alkoxycarbonyloxy.

Examples of heteroalkyl groups are groups of formulas —S—$Y^a$-L, —S—$Y^a$—CO—$NR^aR^b$, —$Y^a$—$NR^c$—CO—$NR^aR^b$, —$Y^a$—$NR^c$—CO—O—$R^d$, —$Y^a$—$NR^c$—CO—$R^d$, —$Y^a$—$NR^c$—CO—$NR^d$-L, —$Y^a$—$NR^c$—CS—$NR^d$-L, —$Y^a$—O—CO—$NR^aR^b$, —$Y^a$—CO—$NR^aR^b$, —O—$Y^a$—CO—$NR^aR^b$, —$Y^a$—$NR^c$—CO-L, —$Y^a$—O—CO—O—$R^c$, —$Y^a$—O—CO—$R^c$, —$Y^a$—CO-L, —$Y^a$—$NR^aR^b$, $R^c$—S—$Y^a$—, $R^a$—N($R^b$)—$Y^a$—, $R^c$—CO—$Y^a$—, $R^c$—O—CO—$Y^a$—, $R^c$—CO—O—$Y^a$—, $R^c$—CO—N($R^b$)—$Y^a$—, $R^a$—N($R^b$)—CO—$Y^a$—, $R^c$—SO—$Y^a$—, $R^c$—$SO_2$—$Y^a$—, —$Y^a$—$NR^c$—$SO_2$—$NR^aR^b$, —$Y^a$—$SO_2$—$NR^aR^b$, —$Y^a$—$NR^c$—$SO_2$—$R^d$, $R^a$—O—CO—N($R^b$)—$Y^a$—, $R^a$—N($R^b$)—C(=$NR^d$)—N($R^c$)—$Y^a$—, $R^c$—S—CO—$Y^a$—, $R^c$—CO—S—$Y^a$—, $R^c$—S—CO—N($R^b$)—$Y^a$—, $R^a$—N($R^b$)—CO—S—$Y^a$—, $R^c$—S—CO—O—$Y^a$—, $R^c$—O—CO—S—$Y^a$—, $R^c$—S—CO—S—$Y^a$—; wherein $R^a$ being a hydrogen atom, a $C_1$-$C_6$alkyl, a $C_2$-$C_6$alkenyl, a $C_2$-$C_6$alkynyl, or is joined to $R^b$ to form a 4- to 10-membered cycloalkyl or heterocycloalkyl; $R^b$ being a hydrogen atom, a $C_1$-$C_6$alkyl, a $C_2$-$C_6$alkenyl or a $C_2$-$C_6$alkynyl, or taken together with $R^a$ to form a 4- to 10-membered cycloalkyl or heterocycloalkyl; $R^c$ being a hydrogen atom, an optionally substituted $C_1$-$C_8$alkyl, an optionally substituted $C_2$-$C_8$alkenyl or an optionally substituted $C_2$-$C_8$alkynyl; $R^d$ being a hydrogen atom, optionally substituted $C_1$-$C_8$alkyl, optionally substituted $C_2$-$C_8$alkenyl or optionally substituted $C_2$-$C_8$alkynyl; L being a cycloalkyl, heterocycloalkyl, alkylcycloalkyl, heteroalkylcycloalkyl, optionally substituted aryl, optionally substituted heteroaryl, aralkyl, or heteroaralkyl; and $Y^a$ being a bond, a $C_1$-$C_6$alkylene, a $C_2$-$C_8$alkenylene or a $C_2$-$C_6$alkynylene group; each heteroalkyl group containing at least one carbon atom and it being possible for one or more hydrogen atoms to have been replaced by fluorine or chlorine atoms. Specific examples of heteroalkyl groups are methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, enol ether, dimethylaminomethyl, dimethylaminoethyl, acetyl, propionyl, butyryloxy, acetyloxy, methoxycarbonyl, ethoxycarbonyl, isobutyrylamino-methyl, N-ethyl-N-methylcarbamoyl and N-methylcarbamoyl. Further examples of heteroalkyl groups are nitrile, isonitrile, cyanate, thiocyanate, isocyanate, isothiocyanate and alkylnitrile groups. An example of a heteroalkylene group is a group of formulas —$CH_2CH(OH)$— or —CONH—.

The expression cycloalkyl preferably refers to a saturated or partially unsaturated cyclic group that contains one or more rings, preferably 1 or 2, containing from 3 to 14 ring carbon atoms, preferably from 3 to 10, more preferably 3, 4, 5, 6 or 7, ring carbon atoms. In an embodiment a partially unsaturated cyclic group has one, two or more double bonds, such as a cycloalkenyl group. The expression cycloalkyl preferably refers furthermore to groups in which one or more hydrogen atoms have been replaced each independently of the others by fluorine, chlorine, bromine or iodine atoms or by OH, =O, SH, =S, $NH_2$, =NH, CN or $NO_2$ groups, thus, for example, cyclic ketones such as, for example, cyclohexanone, 2-cyclohexenone or cyclopentanone. Further specific examples of a cycloalkyl group is a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetralin, cyclopentylcyclohexyl, fluorocyclohexyl or cyclohex-2-enyl group.

The expression heterocycloalkyl preferably refers to a cycloalkyl group as defined above in which one or more, preferably 1, 2 or 3, ring carbon atoms have been replaced each independently of the others by an oxygen, nitrogen, silicon, selenium, phosphorus or sulphur atom, preferably oxygen, sulphur or nitrogen. A heterocycloalkyl group has preferably 1 or 2 ring(s) containing from 3 to 10, more preferably 3, 4, 5, 6 or 7, ring atoms. The expression heterocycloalkyl preferably refers furthermore to groups in which one or more hydrogen atoms have been replaced each independently of the others by fluorine, chlorine, bromine or iodine atoms or by OH, =O, SH, =S, $NH_2$, =NH, CN or $NO_2$ groups. Examples are a piperidyl, piperazinyl, morpholinyl, urotropinyl, pyrrolidinyl, tetrahydrothiophenyl, tetrahydropyranyl, tetrahydrofuryl or 2-pyrazolinyl group and also a lactam, a lactone, a cyclic imide and a cyclic anhydride.

The expression alkylcycloalkyl preferably refers to a group containing both cycloalkyl and also an alkyl, alkenyl or alkynyl group in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10, preferably 3, 4, 5, 6 or 7, carbon atoms, and one or two alkyl, alkenyl or alkynyl groups having 1 or 2 to 6 carbon atoms, the cyclic groups being optionally substituted.

The expression heteroalkylcycloalkyl preferably refers to alkylcycloalkyl groups as defined above in which one or more, preferably 1, 2 or 3, carbon atoms have been replaced each independently of the others by an oxygen, nitrogen, silicon, selenium, phosphorus or sulphur atom, preferably oxygen, sulphur or nitrogen. A heteroalkylcycloalkyl group preferably contains 1 or 2 ring systems having from 3 to 10, preferably 3, 4, 5, 6 or 7, ring atoms, and one or two alkyl, alkenyl, alkynyl or heteroalkyl groups having from 1 or 2 to 6 carbon atoms. Examples of such groups are alkylheterocycloalkyl, heterocycloalkylalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being optionally substituted and saturated or mono-, di- or tri-unsaturated.

The expression aryl or Ar preferably refers to an aromatic group that contains one or more rings containing from 6 to 14 ring carbon atoms, preferably from 6 to 10, more preferably 6, ring carbon atoms. The expression aryl (or Ar) preferably refers furthermore to groups in which one or more hydrogen atoms have been replaced each independently of the others by fluorine, chlorine, bromine or iodine atoms or by OH, SH, $NH_2$, CN or $NO_2$ groups. Examples are a phenyl, naphthyl, biphenyl, 2-fluorophenyl, anilinyl, 3-nitrophenyl or 4-hydroxyphenyl group.

The expression heteroaryl preferably refers to an aromatic group that contains one or more rings containing from 5 to 14 ring atoms, preferably from 5 to 10, more preferably 5 or 6, ring atoms, and contains one or more, preferably 1, 2, 3 or 4, oxygen, nitrogen, phosphorus or sulphur ring atoms, preferably O, S or N. Furthermore, the expression heteroaryl preferably refers to groups in which one or more hydrogen atoms have been replaced each independently of the others by fluorine, chlorine, bromine or iodine atoms or by OH, =O, SH, $NH_2$, =NH, CN or $NO_2$ groups. Examples are 4-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl.

The expression aralkyl preferably refers to a group containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylaryl-cycloalkyl and alkylarylcycloalkenyl groups. Specific examples of aralkyls are toluene, xylene, mesitylene, styrene, benzyl chloride, o-fluorotoluene, 1H-indene, tetralin, dihydro-naphthalene, indanone, phenylcyclopentyl, cumene, cyclohexylphenyl, fluorene and indan. An aralkyl group preferably contains one or two aromatic ring systems, 1 or 2 rings, containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl preferably refers to an aralkyl group as defined above in which one or more, preferably 1, 2, 3 or 4, carbon atoms have been replaced each independently of the others by an oxygen, nitrogen, silicon, selenium, phosphorus, boron or sulphur atom, preferably oxygen, sulphur or nitrogen, that is to say to groups containing both aryl or heteroaryl and also alkyl, alkenyl, alkynyl and/or heteroalkyl and/or cycloalkyl and/or heterocycloalkyl groups in accordance with the above definitions. A heteroaralkyl group preferably contains one or two aromatic ring systems, 1 or 2 rings, containing from 5 or 6 to 10 ring carbon atoms and one or two alkyl, alkenyl and/or alkynyl groups containing 1 or 2 to 6 carbon atoms and/or a cycloalkyl group containing 5 or 6 ring carbon atoms, 1, 2, 3 or 4 of those carbon atoms having been replaced each independently of the others by oxygen, sulphur or nitrogen atoms.

Examples of heteroaralkyl groups are aryloxy, i.e. an univalent radical of the form Ar—O-where Ar is an aryl group; arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl, heteroalkylheteroarylalkyl and heteroarylheteroalkylheterocycloalkyl groups, the cyclic groups being saturated or mono-, di- or tri-unsaturated. Specific examples are a tetrahydroisoquinolinyl, benzoyl, 2- or 3-ethyl-indolyl, 4-methylpyridino, 2-, 3- or 4-methoxyphenyl, 4-ethoxyphenyl, 2-, 3- or 4-carboxy-phenylalkyl group.

The expressions cycloalkyl, heterocycloalkyl, alkylcycloalkyl, heteroalkylcycloalkyl, aryl, heteroaryl, aralkyl and heteroaralkyl also refer to groups in which one or more hydrogen atoms of such groups have been replaced each independently of the others by fluorine, chlorine, bromine or iodine atoms or by OH, =O, SH, =S, $NH_2$, =NH, CN or $NO_2$ groups.

The expression "substituted" as used in connection with any group especially refers to a group in which one or more hydrogen atoms have been replaced each independently of the others by fluorine, chlorine, bromine or iodine atoms or by OH, =O, SH, =S, $NH_2$, =NH, CN or $NO_2$ groups. This expression refers furthermore to a group in which one or more hydrogen atoms have been replaced each independently of the others by an unsubstituted $C_1$-$C_6$alkyl, unsubstituted $C_2$-$C_6$alkenyl, unsubstituted $C_2$-$C_6$alkynyl, unsubstituted $C_1$-$C_6$heteroalkyl, unsubstituted $C_3$-$C_{10}$cycloalkyl, unsubstituted $C_2$-$C_9$heterocycloalkyl, unsubstituted $C_6$-$C_{10}$aryl, unsubstituted $C_1$-$C_9$heteroaryl, unsubstituted $C_7$-$C_{12}$aralkyl or unsubstituted $C_2$-$C_{11}$heteroaralkyl group.

The expression "halogen" or "halogen atom" as preferably used herein means fluorine, chlorine, bromine, iodine.

As used herein a wording defining the limits of a range of length such as, e.g., "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

The present invention preferably relates to a compound of general formula (I), wherein $R^3$ is a hydroxy group.

Preferred is a compound of general formula (I), wherein $R^2$ is hydrogen atom or a hydroxy group.

The present invention preferably relates to a compound, wherein $R^1$ is hydroxy, alkoxy, acyloxy, or heteroaralkyl, wherein the heteroaralkyl can be independently substituted with from 1 to 3 substituents which substituents are each independently selected from halogen atom, hydroxy, nitro, amino, cyano, alkoxy, carboxyl, unsubstituted $C_1$-$C_6$alkyl, sulfonyl, and phosphoryl.

Also preferred is a compound of general formula (I), wherein $R^1$ is hydroxy or optionally substituted aryloxy.

Especially preferred is a compound of general formula (I), wherein $R^1$ is represented by

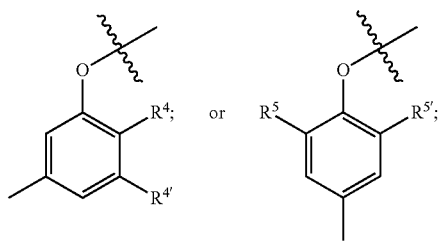

wherein $R^4$, $R^{4'}$, $R^5$, and $R^{5'}$ are each independently selected from a hydrogen atom, a halogen atom, a hydroxy, a nitro, a cyano, an amino, a mercapto, an alkyl, an alkenyl, an alkinyl, and a heteroalkyl group, wherein the alkyl, alkenyl, alkynyl, or heteroalkyl group can be substituted with from 1 to 3 substituents which substituents are each independently selected from halogen atom, hydroxy, nitro, amino, alkoxy, carboxyl, and unsubstituted $C_1$-$C_6$alkyl.

Also preferred is a compound of general formula (I), wherein $R^1$ is a hydroxy group.

It is to be noted that the present invention also encompasses all possible combinations of all preferred embodiments.

Especially preferred, the compound of general formula (I) is selected from one of the following structures:

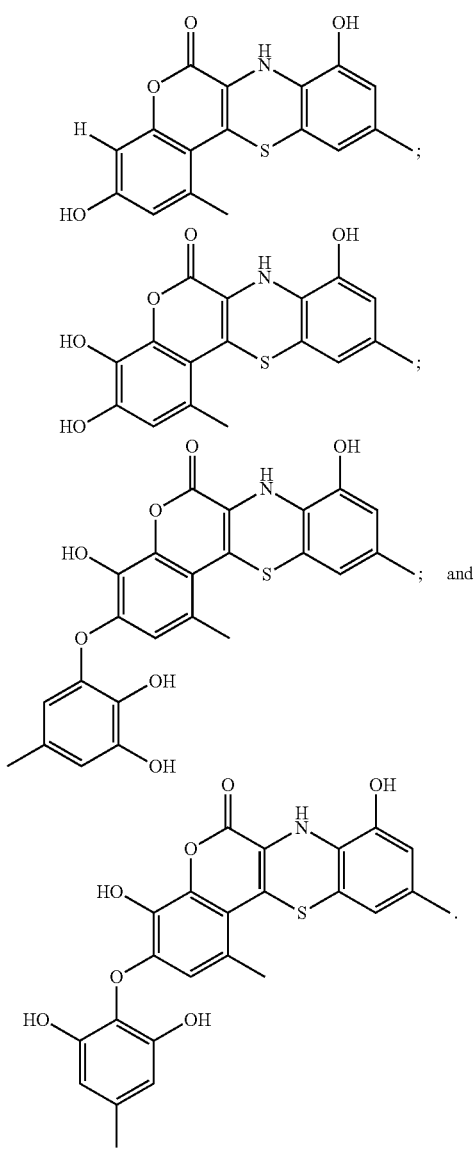

Phaeofungins provided herein exhibit antitumor activity on cultured human tumor cell lines, i.e. an antiproliferative activity with an inhibition constant ($GI_{50}$) and/or a cytotoxic activity with an $IC_{50}$ or $CC_{50}$ in the micromolar range.

The activity and more specifically the pharmacological activity of the phaeofungins according to the present invention can be assessed using appropriate in vitro assays. For instance, the $GI_{50}$, $CC_{50}$, or $IC_{50}$ values of the compounds according to the present invention may be determined via a cytotoxicity and antiproliferative assay of cell growth. Antifungal activities can, for example, be studied qualitatively by agar diffusion tests. Preferred compounds of the invention have values in the micromolar range, still more preferably values in the nanomolar range in the assays mentioned above.

Preferably, the compounds of formula (I) according to the present invention each have one or more pharmacological properties, especially, antiproliferative, antibacterial, antifungal or cytostatic activity, low toxicity, low drug interaction, high bioavailability, especially with regard to oral administration, high metabolic stability, and high solubility.

The therapeutic use of compounds of formula (I), their pharmacologically acceptable salts, prodrugs, solvates and hydrates and also formulations and pharmaceutical compositions containing the same are within the scope of the present invention. The present invention also relates to the use of those compounds of formula (I) as active ingredients in the preparation or manufacture of a medicament, especially, the use of compounds of formula (I), their pharmacologically acceptable salts, prodrugs or solvates and hydrates and also formulations and pharmaceutical compositions for the treatment of fungal or bacterial infections or cancer as well as their use for the preparation of medicaments for the treatment of cancer, fungal or bacterial infections.

The pharmaceutical compositions according to the present invention comprise at least one compound of formula (I) and, optionally, one or more carrier substances, excipients and/or adjuvants. Pharmaceutical compositions may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included in the pharmaceutical compositions provided herein. For instance, the compounds of the invention may advantageously be employed in combination with another antibiotic, anti-fungal, or anti-viral agent, an-anti histamine, a non-steroidal anti-inflammatory drug, a disease modifying anti-rheumatic drug, a cytostatic drug, a drug with smooth muscle activity modulatory activity or mixtures of the aforementioned.

Pharmaceutical compositions may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions such as, e.g., in the treatment of skin conditions such as burns or itch.

Compositions intended for oral use may further comprise one or more components such as sweetening agents, flavoring agents, coloring agents and/or preserving agents in order to provide appealing and palatable preparations. Tablets contain the active ingredient in a mixture with physiologically acceptable excipients that are suitable for the manufacture of tablets. Such excipients include, for example, inert diluents such as, e.g., calcium carbonate, sodium carbonate, lactose, calcium phosphate or sodium phosphate, granulating and disintegrating agents such as, e.g., corn starch or alginic acid, binding agents such as, e.g., starch, gelatin or acacia, and lubricating agents such as, e.g., magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (*Pharmaceutical Press*, London 1993) and Martin (ed.), Remington's Pharmaceutical Sciences.

For the treatment of microbial or fungal infections as well as for the treatment of cancer, the dose of the biologically active compound according to the invention may vary within wide limits and may be adjusted to individual requirements. The required dose may be administered as a single dose or in a plurality of doses. The amount of active ingredient that may be combined with the carrier materials to produce a single dosage form will vary depending upon the host treated and the particular mode of administration. Dosage unit forms will generally contain a sufficient amount of active ingredient. It will be understood, however, that the specific dose level for any particular patient will depend upon a variety of factors including the activity of the specific compound employed, the age, body weight, general health, sex, diet, time of administration, route of administration, and rate of excretion, drug combination, i.e. other drugs being used to treat the patient, and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo.

Phaeofungins provided herein are preferably administered to a patient such as, e.g., a human, orally or topically, and are present within at least one body fluid or tissue of the patient. Accordingly, the present invention further provides methods for treating patients suffering from cancer. As used herein, the term "treatment" encompasses both disease-modifying treatment and symptomatic treatment, either of which may be prophylactic, i.e., before the onset of symptoms, in order to prevent, delay or reduce the severity of symptoms, or therapeutic, i.e., after the onset of symptoms, in order to reduce the severity and/or duration of symptoms. Patients may include but are not limited to primates, especially humans, domesticated companion animals such as dogs, cats, horses, and livestock such as cattle, pigs, sheep, with dosages as described herein.

It is also within the present invention that the compounds according to the invention are used as or for the manufacture of a diagnostic agent, whereby such diagnostic agent is for the diagnosis of the diseases and conditions which can be addressed by the compounds of the present invention for therapeutic purposes as disclosed herein.

For various applications, the compounds of the invention can be labelled by isotopes, fluorescence or luminescence markers, antibodies or antibody fragments, any other affinity label like nanobodies, aptamers, peptides etc., enzymes or enzyme substrates. These labelled compounds of this invention are, for example, useful for mapping the location of tumor cells in vivo, ex vivo, in vitro and in situ such as, e.g. in tissue sections via autoradiography and as radiotracers for positron emission tomography (PET) imaging, single photon emission computerized tomography (SPECT) and the like to characterize those cells in living subjects or other materials. The labelled compounds according to the present invention may be used in therapy, diagnosis and other applications such as research tools in vivo and in vitro, in particular the applications disclosed herein.

Also the following methods for producing a compound of formula (I) lie within the scope of the present invention.

The development of natural product based drugs is often hampered by their structural complexity. This fact precludes facile total synthetic access to analogues or the development of natural product libraries. Therefore, semisynthetic as well as biotechnological approaches are commonly pursued in pharmaceutical research and development (von Nussbaum at al., *Angew. Chem. Int. Ed.* 2006, 45, 5072-5129). A very interesting strategy combines chemical semisynthesis with biosynthesis using genetically engineered microorganisms, a technique which occasionally has been termed mutational biosynthesis or in short mutasynthesis (Review: S. Weist, R. D. Süssmuth, *Appl. Microbiol. Biotechnol.* 2005, 68, 141-150).

For instance, compounds of formula (I) (phaeofungins) can be produced by culturing *A. nidulans* lacking the *nidulans* n-acetyltransferase B gene. It is understood that the production of phaeofungins is not limited to the use of the particular organism described herein, which is given for illustrative purpose only. The invention also includes the use of any mutants which are capable of producing phaeofungins including natural mutants as well as artificial mutants, e.g. genetically manipulated mutants and the expression of the gene cluster responsible for biosynthesis in a producer strain or by heterologous expression in host strains. *A. nidulans* strain A1153ΔnnaB has been deposited at DSMZ; accession number DSM 24940.

Phaeofungins are produced in liquid culture, by growing the respective microorganism in media containing one or several different carbon sources, and one or different nitrogen sources. Also salts are essential for growth and production. Suitable carbon sources are different mono-, di-, and polysaccharides like maltose, glucose or carbon from amino acids like peptones. Nitrogen sources are ammonium, nitrate, urea, chitin or nitrogen from amino acids. The following inorganic ions support the growth or are essential in synthetic media: Mg-ions, Ca-ions, Fe-ions, Mn-ions, Zn-ions, K-ions, sulfate-ions, Cl-ions, phosphate-ions.

Temperatures for growth and production are between 10° C. to 40° C., preferred temperatures are between 30° C. and 38° C., especially at 37° C. The pH of the culture solution is from 5 to 8, preferably 6.5 and 7.5, especially at pH 7.2.

Phaeofungins can also be obtained by chemical synthesis. For example, the synthesis of the benzopyranobenzothiazin-6-one scaffold has been reported by Reddy and Darbarwar (*Sulfur Lett.* 1984, 2, 183). Accordingly, phaeofungins can also be prepared using usual chemical reactions and synthesis methods known to a person skilled in the art.

Figure 1:
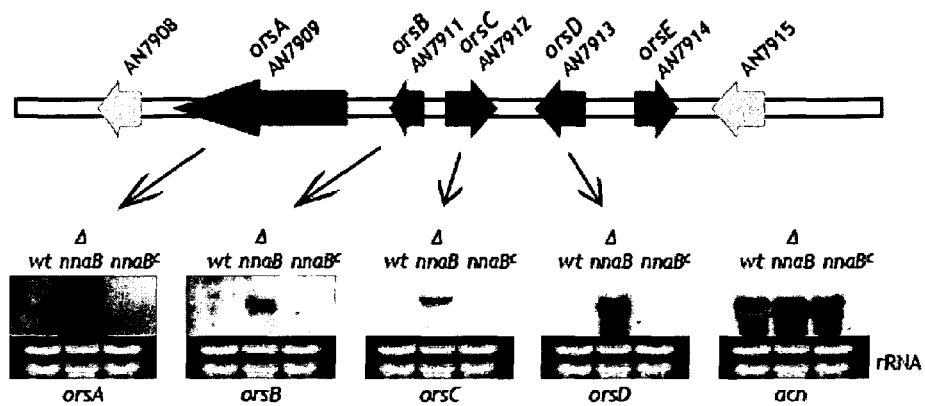
FIG. 1. Secondary metabolite gene cluster activation in ΔnaaA strain. (A) Northern blot analysis of the ors gene cluster genes in wild type (wt), ΔnnaB mutant and complemented strain incubated for 29 h in malt medium. Numbers above the arrows indicate annotated ORFs. The actin gene (acn) was used as a control/reference. (B) Relative quantity of the mRNA steady-state level determined by qRT-PCR of orsA-C. Quantity is given as log 2 of $-\Delta\Delta Ct$. AN7908 and AN7915 flanking the ors gene cluster were analyzed as control genes. (I) Cultivation of wt, (II) ΔnnaB, and (III) ΔnnaB for 29 h in malt medium. Expression level in wt was set as 1.
Figure 1:
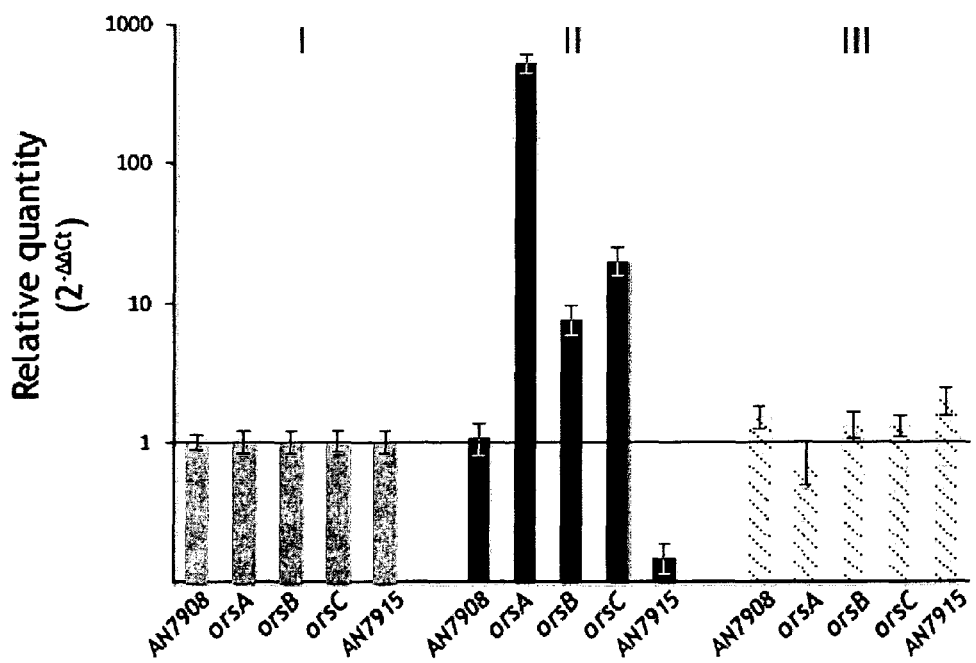
Figure 2:
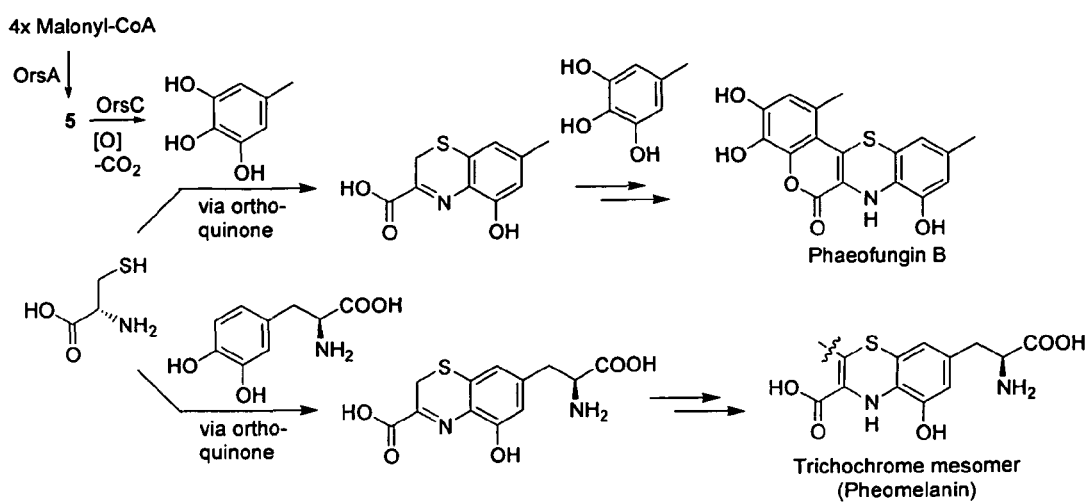
FIG. 2. Structural similarity of the pheomelanin and phaeofungin chromophores and plausible model for phaeofungin biosynthesis.
Figure 3A:
FIGS. 3A and 3B. International Forms from the Budapest Treaty on the international recognition of the deposit of microorganisms for the purposes of patent procedure verifying receipt (FIG. 3A) and viability (FIG. 3B) of Accession Number DSM 24940.
Figure 3B:

The present invention is now further illustrated by the following examples from which further features, embodiments and advantages of the present invention may be taken. However, these examples are by no means construed to be limiting to the present invention.

EXAMPLES

All reagents were purchased from commercial suppliers and used without further purification.

Material and Methods

Analytical HPLC was performed on a Shimadzu LC-10Avp series HPLC system consisting of an autosampler, high pressure pumps, column oven and DAD. HPLC conditions: C18 column (Eurospher 100-5 250×4.6 mm) and gradient elution (MeCN/0.1% TFA 0.5/99.5 in 30 min to MeCN/ 0.1% TFA 100/0, MeCN 100% for 10 min), flow rate 1 mL min$^{-1}$. Preparative HPLC was performed on a Shimadzu LC-8a series HPLC system with DAD. NMR spectra were recorded on Bruker Avance DRX 500 and DRX 600 instruments. Spectra were referenced to the residual solvent signals.

Strain

The *Aspergillus nidulans* strain A1153ΔnnaB (Genotype: nnaB:argB2 yA1 pabaA1 pyroA4 nkuA:bar) was used. *A. nidulans* strain A1153 contains the deletion of the nkuA gene that leads to reduced non-homologous recombination. Deletions strains were obtained by transformation (Ballance and Turner, Gene 1985, 36, 321) using the argB or the pabaA gene of *A. nidulans* as selectable marker. Deletions cassettes were produced as described in Szewczyk et al., Nat. Protoc. 2006, 1, 3111. Southern blot analysis were carried out to prove correct integration of the deletion cassette in the locus of interest. The *A. nidulans* ΔnnaB mutant (A1153ΔnnaB) is impaired in posttranslational protein modification, since it lacks the gene to nnaB (*nidulans* n-acetyltransferase B) and shows changes in phenotype: slow growth and a change in color from yellow (wild type) to red/orange mycelium (mutant). In addition to the obvious phenotypic changes, the *A. nidulans* ΔnnaB mutant also shows a significantly increased production of secondary metabolites compared to the wild type. This effect was clearly correlated to the absence of nnaB since the complemented strain, nnaB$^c$, fully restored the wild-type phenotype as well as the metabolic fingerprint.

Generation of Deletion Cassettes

Deletion cassettes were constructed according to Szewczyk et al. (loc.cit.). About 1500 bp long DNA fragments flanking the ORF of interest were amplified using genomic DNA of *A. nidulans* and fused to the argB deletion cassette (Szewczyk et al., loc. cit.) or the pabaA deletion cassette (Tuncher et al., J. Mol. Biol. 2005, 352, 517.) The deletion primers were used for fusion-PCR to assemble flanking regions and deletion cassette.

Preparation of Chromosomal DNA and Southern Blot Analysis

For isolation of chromosomal DNA of *A. nidulans* the protocol of Schroeckh et al., *Proc. Natl. Acad. Sci.* USA 2009, 106, 14558, was followed using the MasterPure Yeast DNA purification Kit with the modifications of Wickes, in *Epicentre forum*, Vol. 11, 2004, p. 7. Probes for Southern blots were labeled with digoxygenin-11-dUTP. Fluorescence signals were detected with Super RX x-ray films (Fuji) (Schroeckh et al., loc.cit.).

Northern Blot Analysis

Isolation of total RNA from *A. nidulans* using the TriSURE reagent (Bioline) and Northern blot analyses were carried out as previously described (Schroeckh et al., loc.cit.). Probes were labeled with digoxygenin-11-dUTP.

qRT-PCR qRT-PCR analysis was performed as described before (Schroeckh et al., loc.cit.). In brief, DNAse treated total RNA was reverse transcribed into cDNA using Superscript III reverse transcriptase (Invitrogen). Applied Biosystems StepOne Real-Time PCR system was used with the GeneAmp Fast PCR Master Mix (Applied Biosystems) to amplify targets. EvaGreen was taken as labeling agent. Each sample was measured in triplicate and the *A. nidulans* β-actin was used as internal standard for calculation of expression levels. qRT-PCR results were analyzed using StepOne software (version 2.0, Applied Biosystems) and the relative expression levels for each sample were obtained by the ΔΔCt method with normalization to β-actin using the formula $2^{-(CIAN79xx-Ctacn)}$.

Media and Cultivation Conditions

*A. nidulans* was incubated in malt medium (20 g L$^{-1}$ malt extract, Difco; 2 g L$^{-1}$ yeast extract, Ohly; 10 g L$^{-1}$ glucose; 0.5 g L$^{-1}$ (NH$_4$)$_2$HPO$_4$; pH 7.2). Required supplements were added as follows: arginine (final concentration 50 μM), p-aminobenzoic acid (3 μg mL$^{-1}$), pyridoxine HCl (5 μg mL$^{-1}$). 1.5$^6$ spores mL$^{-1}$ malt medium were inoculated and incubated at 37° C. for 40 h with shaking (200 rpm). Harvesting of mycelia for RNA isolation was done after 29 h incubation.

Extraction and Isolation of Compounds

The entire fermentation broth was exhaustively extracted with ethyl acetate and the combined extracts were concentrated under reduced pressure. The crude extract was separated by size exclusion chromatography using Sephadex LH-20 (Pharmacia) and methanol as an eluent. Metabolite-containing fractions were further purified by two runs of preparative HPLC using a Grom Saphir C18 column (250×25 mm) with a flow rate of 10 mL min$^{-1}$ and UV detection at 218 and 278 nm. For the isolation of phaeofungins A and C first a gradient mode with MeCN/H$_2$O from 50% MeCN to 83% MeCN in 20 min, then 83% MeCN for 10 min was applied, and second an isocratic mode with MeCN/H$_2$O 75/25. Phaeofungins B and D were separated by two steps of isocratic preparative HPLC with MeCN/H$_2$O 75/25 and 66/34, respectively.

Analytical Data of Novel Metabolites

Phaeofungin A.

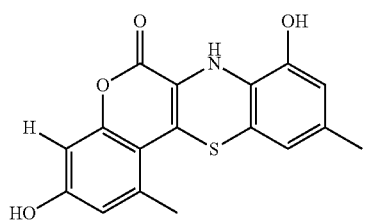 [SMILES: Cc1cc(O)c2c(c1)Sc1c(c(=O)oc3cc(O)cc(C)c13)N2]

$^1$H NMR (d$_6$-DMSO, 600 MHz, J in Hz): 10.34 (1H, s, 3-OH), 10.23 (1H, s, 8-OH), 6.59 (1H, d, J=2.5, H-2), 6.57 (1H, d, J=2.5, H-4), 6.51 (1H, s, NH), 6.46 (1H, d, H-9), 6.33 (1H, d, H-11), 2.74 (3H, s, H-13), 2.08 (3H, s, H-14). $^{13}$C

NMR (d$_6$-DMSO, 150 MHz): 157.6 (C-3), 154.6 (C-6), 151.6 (C-4a), 143.6 (C-8), 136.5 (C-1), 133.2 (C-10), 126.9 (C-7a), 123.0/122.9 (C-6a/C-12a), 117.5 (C-2), 117.5 (C-11), 115.6 (C-9), 114.0 (C-11a), 109.2 (C-12b), 101.3 (C-4), 24.2 (C-13), 20.4 (C-14) UV (DAD) $\lambda_{max}$=218, 279, 315 (sh), 433 nm. (−)-ESI-MS m/z 326 [M−H]$^-$, (+)-ESI-MS m/z 328 [M+H]$^+$. HRESI-MS: m/z [M−H]$^-$=326.0488 (calcd. for C$_{17}$H$_{12}$NO$_4$S 326.0493)

Phaeofungin B.

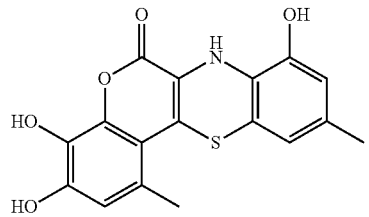 [SMILES: Cc1cc(O)c2c(c1)Sc1c(c(=O)oc3c(O)c(O)cc(C)c13)N2]

$^1$H NMR (d$_6$-DMSO, 500 MHz, J in Hz): 10.14 (1H, s, 8-OH), 9.79 (1H, s, 3-OH), 9.11 (1H, s, 4-OH), 6.59 (1H, s, H-2), 6.53 (1H, s, NH), 6.47 (1H, s, H-9), 6.33 (1H, s, H-11), 2.67 (3H, s, H-13), 2.09 (3H, s, H-14). $^{13}$C NMR (d$_8$-DMSO, 125 MHz): 154.4 (C-6), 146.0 (C-3), 143.5 (C-8), 140.5 (C-4a), 133.0 (C-10), 130.7 (C-4), 126.8 (C-7a), 124.4 (C-1), 123.3 (C-12a), 122.4 (C-6a), 117.3 (C-11), 116.8 (C-2), 115.5 (C-9), 113.9 (C-11a), 109.4 (C-12b), 23.5 (C-13), 20.3 (C-14) UV (DAD) $\lambda_{max}$=215, 279, 316 (sh), 432 nm. (−)-ESI-MS m/z 342 [M−H]$^-$, (+)-ESI-MS m/z 344 [M+H]$^+$. HRESI-MS: m/z [M+H]$^+$=344.0590 (calcd. for C$_{17}$H$_{14}$NO$_5$S 344.0587)

Phaeofungin C.

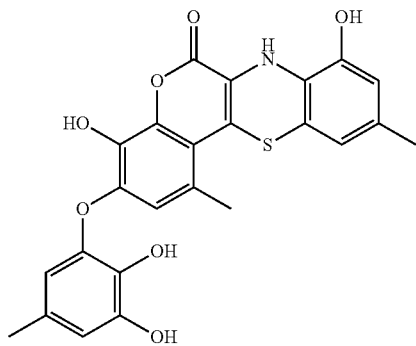

$^1$H NMR (d$_6$-DMSO, 600 MHz, J in Hz): 10.28 (1H, br s, OH), 10.18 (1H, s, 8-OH), 8.88 (1H, s, 3'-OH), 8.36 (1H, br s, OH), 6.75 (1H, s, H-2), 6.53 (1H, s, NH), 6.47 (1H, s, H-9), 6.35 (1H, s, H-11), 6.23 (1H, d, H-4'), 5.64 (1H, d, H-6'), 2.75 (3H, s, H-13), 2.09 (3H, s, H-14), 1.94 (3H, s, H-7'). $^{13}$C NMR (d$_6$-DMSO, 150 MHz): 154.0 (C-6), 150.2 (C-3), 146.4 (C-1'), 146.3 (C-3'), 144.7 (C-4a), 143.6 (C-8), 133.3 (C-10), 131.7 (C-2'), 131.3 (C-1), 127.4 (C-4), 126.9 (C-5'), 126.7 (C-7a), 123.1 (C-6a), 122.9 (C-12a), 117.6 (C-2), 117.4 (C-11), 115.6 (C-9), 113.8 (C-11a), 110.4 (C-4'), 109.9 (C-12b), 104.8 (C-6'), 24.0 (C-13), 20.6 (C-7'), 20.3 (C-14) UV (DAD) $\lambda_{max}$=214, 279, 316 (sh), 433 nm. (−)-ESI-MS m/z 464 [M−H]$^-$, (+)-ESI-MS m/z 488 [M+Na]$^+$. HRESI-MS: m/z [M−H]$^-$=464.0815 (calcd. for C$_{24}$H$_{18}$NO$_7$S 464.0809)

Phaeofungin D.

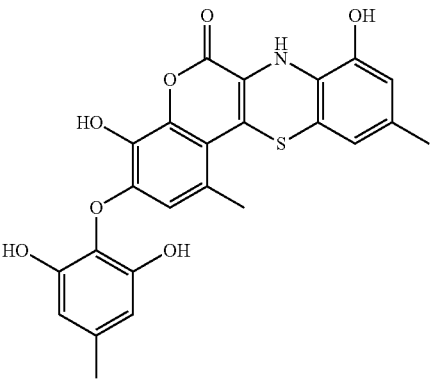 [SMILES: Cc1cc(O)c(Oc2cc(C)c3c4c(c(=O)oc3c2O)Nc2c(O)cc(C)cc2S4)c(O)c1]

$^1$H NMR (d$_8$-DMSO, 600 MHz, J in Hz): 10.18 (1H, s, 8-OH), 9.45 (1H, s, 4-OH), 9.29 (2H, s, 1'-OH/3'-OH), 6.59 (1H, s, NH), 6.47 (1H, s, H-9), 6.31 (1H, s, H-11), 6.22 (2H, s, H-4'/H-6'), 6.16 (1H, s, H-2), 2.58 (3H, s, H-13), 2.15 (3H, s, H-7'), 2.08 (3H, s, H-14). $^{13}$C NMR (d$_6$-DMSO, 150 MHz): 154.3 (C-6), 150.4 (C-1'), 150.4 (C-3'), 146.1 (C-3), 143.5 (C-8), 140.0 (C-4a), 134.8 (C-5'), 133.3 (C-10), 132.0 (C-4), 126.9 (C-2'), 126.6 (C-7a), 123.4 (C-1), 123.3 (C-6a), 122.4 (C-12a), 117.4 (C-11), 115.5 (C-9), 113.9 (C-2), 113.9 (C-11a), 111.2 (C-12b), 108.2 (C-4'), 108.2 (C-6'), 23.8 (C-13), 21.0 (C-7'), 20.3 (C-14) UV (DAD) $\lambda_{max}$=218, 279, 315 (sh), 432 nm. (−)-ESI-MS m/z 464 [M−H]$^-$, (+)-ESI-MS m/z 488 [M+Na]$^+$. HRESI-MS: m/z [M−H]$^-$=464.0818 (calcd. for C$_{24}$H$_{18}$NO$_7$S 464.0809)

Bioassays

HeLa cells were used for the cytotoxic assay, HUVEC and K-562 cells were taken for the antiproliferative assay. The assays were conducted with phaeofungin C as described previously (Krauth et al., Bioorg. Med. Chem. 2010, 18, 1816-1821; Abdou et al., Phytochemistry 2010, 71, 110-116). Dose-response curves and IC$_{50}$ values were then plotted and estimated, respectively.

It was found that phaeofungin C effectively inhibits the proliferation of HUVEC (GI$_{50}$ 7.5 μM) and K-562 human leukemia cell lines (GI$_{50}$ 2.4 μM). Furthermore, phaeofungin C shows cytotoxic effects against HeLa cells with an IC$_{50}$ of 10 μM.

The invention claimed is:

1. A compound of formula (I):

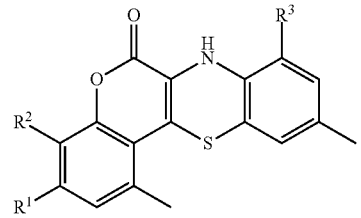

or a pharmacologically acceptable salt, solvate, hydrate or a pharmacologically acceptable formulation thereof, wherein R$^1$ is a hydrogen atom, a halogen atom, a hydroxy, a nitro, a cyano, an amino, a mercapto, an alkyl, an alkenyl, an alkinyl, a heteroalkyl, a cycloalkyl, a heterocycloalkyl, an alkylcycloalkyl, a heteroalkylcycloalkyl, an aryl, a heteroaryl, an aralkyl or a heteroaralkyl group, wherein the alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group can be substituted with from 1 to 3 substituents which substituents are each independently selected from halogen atom, hydroxy, nitro, amino, alkoxy, carboxyl, alkyl, alkynyl, alkenyl, aryl, sulfonyl, phosphoryl, or R$^1$ is taken together with R$^2$ to form a 5- to 8-membered carbocyclic or heterocyclic ring that is substituted with from 0 to 3 substituents which substituents are each independently selected from halogen atom, hydroxy, nitro, amino, alkoxy, carboxyl, alkyl, alkynyl, alkenyl, or aryl;

R$^2$ is a hydrogen atom, a halogen atom, a hydroxy, an amino, a mercapto, an alkyl, an alkenyl, an alkinyl, a heteroalkyl, a cycloalkyl, a heterocycloalkyl, an alkylcycloalkyl, a heteroalkylcycloalkyl, an aryl, a heteroaryl, an aralkyl or a heteroaralkyl group, wherein the alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group can be substituted with from 1 to 3 substituents which substituents are each independently selected from halogen atom, hydroxy, nitro, amino, alkoxy, carboxyl, alkyl, alkynyl, alkenyl, aryl, sulfonyl, phosphoryl;

R$^3$ is a hydroxyl group.

2. The compound according to claim 1, wherein R$^2$ is hydrogen atom or a hydroxy group.

3. The compound according to claim 1, wherein R$^1$ is hydroxy, alkoxy, acyloxy, or heteroaralkyl, wherein the heteroaralkyl can be independently substituted with from 1 to 3 substituents which substituents are each independently selected from halogen atom, hydroxy, nitro, amino, cyano, alkoxy, carboxyl, unsubstituted C$_1$-C$_6$alkyl, sulfonyl, and phosphoryl.

4. The compound according to claim 1, wherein R$^1$ is hydroxy or optionally substituted aryloxy.

5. The compound according to claim 1, wherein R$^1$ is represented by

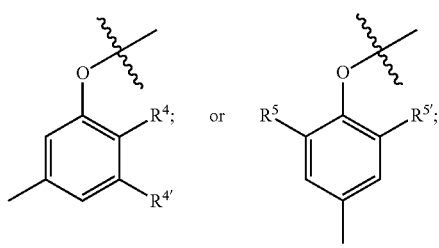

wherein R$^4$, R$^{4'}$, R$^5$, and R$^{5'}$ are each independently selected from a hydrogen atom, a halogen atom, a hydroxy, a nitro, a cyano, an amino, a mercapto, an alkyl, an alkenyl, an alkinyl, and a heteroalkyl group, wherein the alkyl, alkenyl, alkynyl, or heteroalkyl group can be substituted with from 1 to 3 substituents which substituents are each independently selected from halogen atom, hydroxy, nitro, amino, alkoxy, carboxyl, and unsubstituted C$_1$-C$_6$alkyl.

6. The compound according to claim 1, wherein R$^1$ is a hydroxy group.

7. The compound according to claim 1, wherein the compound is selected from one of the following structures:

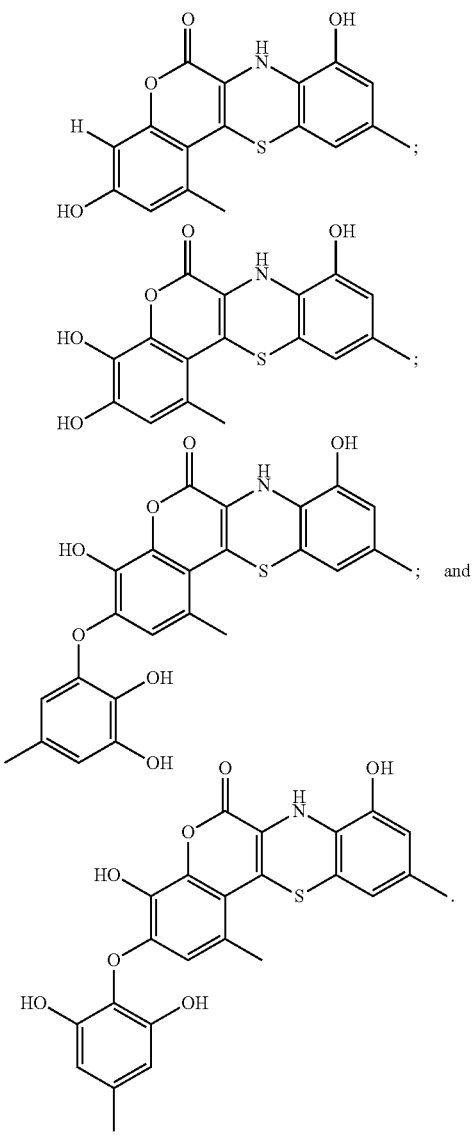

8. A pharmaceutical composition that comprises a compound of claim 1 or a pharmacologically acceptable salt thereof and, optionally, at least one carrier substance, at least one adjuvant, or a combination thereof.

9. A method for the preparation of a compound of formula (I), the method comprising the steps of:
  (a) fermenting *Aspergillus nidulans* strain A1153ΔnnaB (DSMZ accession number DSM 24940); and
  (b) separating and retaining the compound from the culture broth.

10. The method according to claim 9, wherein the compound is selected from any of

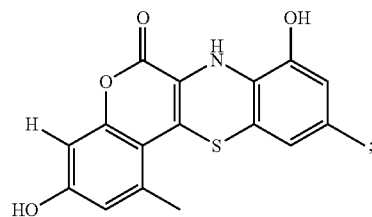

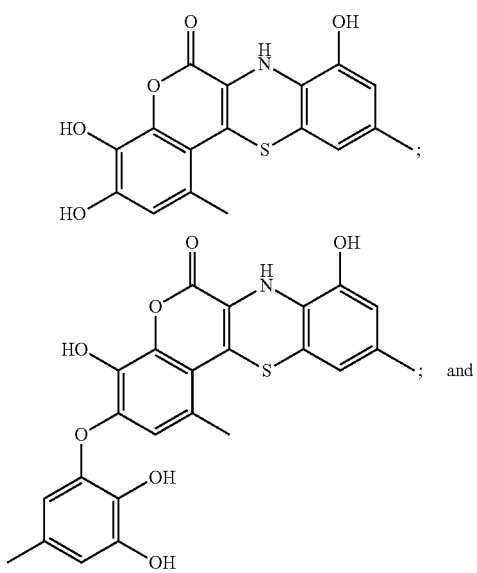
; and

11. A method for treating a bacterial infection or a fungal infection, comprising administering a compound of claim 1 to a subject in need of treatment thereby treating the subject's bacterial infection or fungal infection.

12. A method for treating a bacterial infection or a fungal infection, comprising administering a pharmaceutical composition of claim 8 to a subject in need of treatment thereby treating the subject's bacterial infection or fungal infection.

* * * * *